United States Patent [19]

Annis

[11] Patent Number: 4,659,329
[45] Date of Patent: Apr. 21, 1987

[54] LIQUID DRAINAGE SYSTEM
[75] Inventor: Larry D. Annis, Elgin, Ill.
[73] Assignee: The Kendall Company, Boston, Mass.
[21] Appl. No.: 870,601
[22] Filed: Jun. 4, 1986

Related U.S. Application Data

[63] Continuation of Ser. No. 635,090, Jul. 27, 1984, abandoned.

[51] Int. Cl.⁴ .............................................. A61M 5/32
[52] U.S. Cl. ................................. 604/180; 604/327; 128/DIG. 26
[58] Field of Search .............................. 604/174–180, 604/327–331; 128/DIG. 6, DIG. 26, 133

[56] References Cited

U.S. PATENT DOCUMENTS

| | | | |
|---|---|---|---|
| 3,568,679 | 3/1971 | Reif | 604/180 |
| 3,860,006 | 1/1975 | Patel | 128/347 |
| 4,029,103 | 6/1977 | McConnell | 128/DIG. 26 |
| 4,149,539 | 4/1979 | Cianci | 128/DIG. 26 |
| 4,261,363 | 4/1981 | Russo | 604/174 |
| 4,397,641 | 8/1983 | Jacobs | 604/180 |
| 4,419,094 | 12/1983 | Patel | 604/93 |
| 4,435,174 | 3/1984 | Redmond et al. | 604/174 |
| 4,517,971 | 5/1985 | Sorbonne | 128/DIG. 26 |
| 4,533,349 | 8/1985 | Bork | 604/174 |

Primary Examiner—C. Fred Rosenbaum
Assistant Examiner—Mario Costantino
Attorney, Agent, or Firm—Powell L. Sprunger

[57] ABSTRACT

A liquid drainage system comprising, an elongated catheter having a lumen, a distal end for placement in a patient, and a proximal end. The system has a retaining assembly comprising, a base plate for placement adjacent the patient, and an upright wall extending substantially peripherally around the base plate and having an opening, with the base plate having an aperture to receive the catheter and an upright retaining member having a groove extending from the aperture to receive the catheter in the groove. The catheter is wound in at least one coil inside the wall and extends toward the wall opening.

11 Claims, 2 Drawing Figures

LIQUID DRAINAGE SYSTEM

This is a continuation of application Ser. No. 635,090, filed July 27, 1984, now abandoned.

BACKGROUND OF THE INVENTION

The present invention relates to liquid drainage systems.

Liquid drainage systems for draining urine from a patient's bladder are known. In one form, such systems have a suprapubic catheter extending through the abdominal wall to the bladder, and urine drains from the bladder through the catheter into a collection bag connected to a proximal end of the catheter outside the patient's body. However, it has been found that the length of catheter outside the patient's body has a tendency to kink or twist which may close a lumen in the catheter and render the system inoperable.

SUMMARY OF THE INVENTION

A principal feature of the present invention is the provision of an improved drainage system for a patient.

The drainage system comprises, an elongated catheter having a lumen, a distal end for placement in the patient, and a proximal end. The system has a retaining assembly comprising, a base plate for placement adjacent the patient, and an upright wall extending substantially peripherally around the base plate and having an opening, with the base plate having an aperture to receive the catheter and an upright retaining member having a groove extending from the aperture to receive the catheter in the groove. The catheter is wound in at least one coil inside the wall and extends toward the wall opening.

A feature of the present invention is that the retaining assembly prevents kinking or twisting of the catheter outside the patient's body.

Another feature of the invention is that the system thus prevents blocking of the catheter which otherwise would render the system inoperable.

A further feature of the invention is the provision of a lid releasably locked to the wall in order to retain the catheter in the retaining assembly.

Yet another feature of the invention is the provision of a plurality of upright pins on the base plate for retaining the catheter adjacent the wall opening and prevent twisting of the catheter in this region.

Further features will become more fully apparent in the following description of the embodiments of this invention and from the appended claims.

DESCRIPTION OF THE PREFERRED EMBODIMENTS

Figures 1, 2:
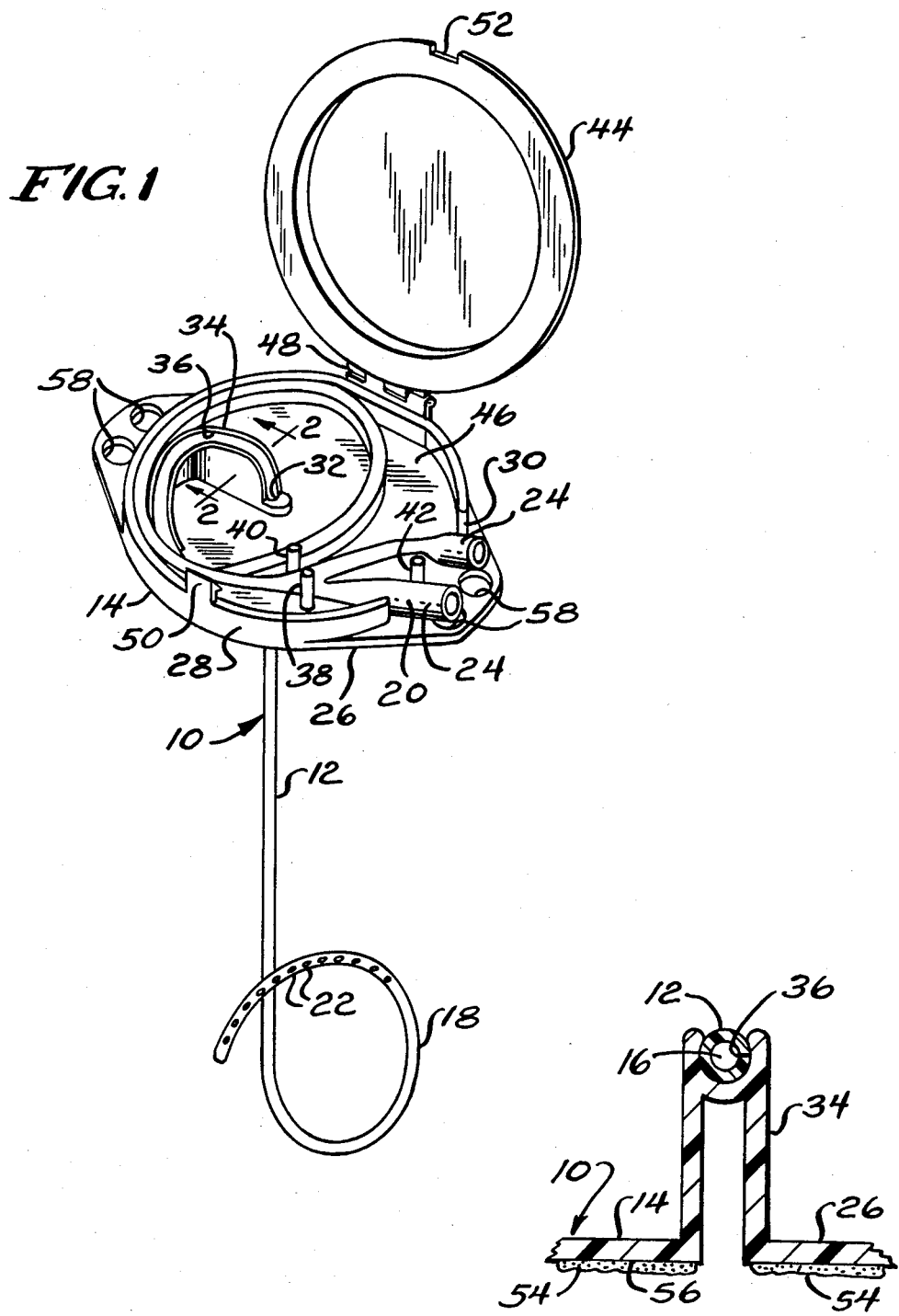
FIG. 1 is a perspective view of a liquid drainage system of the present invention.
FIG. 2 is a fragmentary sectional view taken substantially as indicated along the line 2—2 of FIG. 1.

Referring now to FIGS. 1 and 2, there is shown a liquid drainage system generally designated 10 having an elongated suprapubic catheter 12 in a retaining assembly 14. The catheter 12 has a lumen 16 extending through the catheter 12, a distal end 18 in the form of a coil, and a proximal end 20. As shown, the distal end 18 has a plurality of apertures 22 extending along the catheter 12 and communicating with the lumen 16, and the catheter 12 in a preferred form has a Y-connection 24 at the proximal end 20 of the catheter 12. In use, the distal end 18 of the catheter 12 is located in the patient's bladder, and urine drains through the apertures 22 and lumen 16 to the proximal end 20 of the catheter 12, after which the urine passes through a suitable drainage tube (not shown) to a collection bag (not shown) for retention therein.

The retaining assembly 14 has a base plate 26 for placement adjacent the patient's body, and an upright wall 28 extending substantially peripherally around the base plate 26 and having an opening 30. The base plate 26 has an aperture 32 extending through the base plate 26 to receive the catheter 12. The base plate 26 also has an upright retaining member 34 having a groove 36 extending from the aperture 32 to snugly receive the catheter 12 in the groove 36. As shown, the catheter 12 is wound at least once, and preferably twice, in a coil inside the wall 28, and the proximal end 20 of the catheter 12 is preferably located adjacent the opening 30. The retaining member 34 is preferably curved in the direction the catheter is wound inside the wall 28.

The base plate 26 has a pair of spaced upright pins 38 and 40 to receive the proximal end 20 of the catheter 12 and retain the catheter 12 in place inside the wall 28. Also, the base plate 26 preferably has a third upright pin 42 located intermediate the Y-connection 24 in order to prevent twisting of the proximal end 20 of the catheter 12.

The retaining assembly 14 has a lid 44 for closing a cavity 46 inside the wall 28. As shown, one end of the lid 44 has a pivotal connection 48 for pivotally connecting the lid 44 to the wall 28. At the other end of the wall 28, the wall 28 has a hooked flange 50 which is releasably received in a notch 52 of the lid 44 in order to releasably lock the lid 44 onto the wall 28.

The retaining assembly 14 preferably has means for securing the base plate 26 onto the patient's skin after placement of the catheter 12 in the bladder. In one form, the base plate 26 has adhesive 54 on a lower surface 56 of the base plate 26 to secure the base plate 26 onto the patient's skin. In an alternative form, the base plate 26 has a plurality of apertures 58 extending therethrough to receive sutures and secure the base plate 26 onto the patient'skin.

Thus, in accordance with the present invention a liquid drainage system 10 is disclosed in which a suprapubic catheter 12 is wound inside a retaining assembly 14 and is secured in place in order to prevent kinking or twisting of the catheter outside the patient's body, which otherwise would render the system inoperable.

The foregoing detailed description is given for clearness of understanding only, and no unnecessary limitations should be understood therefrom, as modifications will be obvious to those skilled in the art.

I claim:

1. A liquid drainage system, comprising:
  an elongated catheter having a lumen, a distal end for placement in a patient, and a proximal end; and
  a retaining assembly comprising, a base plate for placement adjacent the patient, an upright outer wall extending substantially peripherally around the base plate to define a space and having an opening in the wall, said base plate having a lower surface, an aperture in the base plate approximately the size of the catheter to receive the catheter and an upright retaining member within the space defined by the wall and attached to the base plate adjacent the aperture, the retaining member having an upper surface defining a groove between opposed sides of the retaining member and extending directly from said aperture to receive the catheter in the groove, said catheter being wound around the retaining member only within the wall in at least one coil inside the wall and extending toward the wall opening.

2. The device of claim 1 wherein the proximal end of the catheter is located adjacent the wall opening.

3. The device of claim 1 including a pair of upright spaced pins on the base plate to receive the catheter.

4. The device of claim 1 wherein the catheter includes a Y-connection having a pair of branches at the proximal end of the catheter.

5. The device of claim 4 wherein the Y-connection is located adjacent the wall opening, and including an upright pin on the base plate adjacent the wall opening located intermediate the branches of the Y-connection.

6. The device of claim 1 including means for securing the base plate to the patient.

7. The device of claim 6 wherein the securing means comprises adhesive on the lower surface of the base plate.

8. The device of claim 6 wherein the securing means comprises a plurality of apertures in the base plate to receive sutures.

9. The device of claim 1 including a lid for covering the space intermediate the wall.

10. The device of claim 9 including means for releasably locking the lid in a closure position over the wall.

11. The device of claim 1 wherein the retaining member is curved in the direction the catheter is wound inside the wall.

* * * * *